United States Patent
Brigstock et al.

[11] Patent Number: 5,876,730
[45] Date of Patent: Mar. 2, 1999

[54] HEPARIN-BINDING GROWTH FACTOR (HBGF) POLYPEPTIDES

[75] Inventors: David R. Brigstock, Dublin; Paul A. Harding, Cincinnati, both of Ohio

[73] Assignee: Childrens Hospital Research Foundation, Columbus, Ohio

[21] Appl. No.: 908,526

[22] Filed: Aug. 7, 1997

[51] Int. Cl.$^6$ ............................... A61K 38/18
[52] U.S. Cl. ............... 424/198.1; 530/300; 530/350; 530/399; 530/850; 435/69.4; 930/120
[58] Field of Search ............... 530/300, 350, 530/399, 850, 23.5; 930/120; 435/69.4; 424/198.1

[56] References Cited

U.S. PATENT DOCUMENTS 5,408,040   4/1995   Grotendorst et al. .................. 530/399

OTHER PUBLICATIONS

Brigstock et al., J. Biological Chemistry 272:20275–20282, 1997.
G.R. Grotendorst, Cytokine Growth Factor Reviews 8(3):171–179, 1997.
Brigstock et al., J. Reprod. Fert. 85:747–758, 1989.
G.Y. Kim et al., Biology of Reproduction 52:561–571, 1995.
Campochiaro et al., "Retinal Pigment Epithalial Cells Produce PDGF–like Proteins and Secrete them into their Media", *Exp. Eye Res.*, (1989) 49:217–227
Shimokado et al., "A Significant Part of Macrophage–Derived Growth Factor Consists of at Least Two Forms of PDGF", *Cell*, 43:277–286, Nov.1985.
Matsuoka et al., "Two peptides related to platelet–derived growth factor are present in human wound field", *Proc. Natl. Acad. Sci. USA*, vol. 86, pp. 4416–4420, Jun. 1989.
Ryseck at al., "Structure, Mapping and Expression of fisp–12, a Growth Factor–inducible Gene Encoding a Secreted Cysteine–rich Protein", *Cell*, Vol. 2 pp. 225–233, May 1991.

*Primary Examiner*—Lorraine Spector
*Attorney, Agent, or Firm*—Fish & Richardson P.C.

[57] ABSTRACT

Substantially pure heparin-binding growth factor polypeptides (HBGFs), nucleic acids encoding the HBGFs and antibodies which bind to the HBGFs of the invention are provided. The HBGF polypeptides are useful in methods for the induction of bone, cartilage and tissue formation, growth and development of the endometrium and in the acceleration of wound healing. HBGF is related to Connective Tissue Growth Factor (CTGF).

9 Claims, 5 Drawing Sheets

HEPARIN-BINDING GROWTH FACTOR (HBGF) POLYPEPTIDES

FIELD OF THE INVENTION

This invention relates generally to the field of growth factors, more specifically to heparin-binding growth factors (HBGF).

BACKGROUND OF THE INVENTION

Growth factors are a class of polypeptides that stimulate target cells to proliferate, differentiate and organize in developing tissues. The action of growth factors is dependent on their binding to specific receptors which stimulates a signaling event within the cell. Examples of growth factors include platelet-derived growth factor (PDGF), insulin-like growth factor (IGF-I, IGF-II), transforming growth factor beta (TGF-β), transforming growth factor alpha (TGF-α), epidermal growth factor (EGF), acidic and basic fibroblast growth factors (aFGF, bFGF) and connective tissue growth factor (CTGF) which are known to stimulate cells to proliferate.

PDGF is a cationic, heat stable protein found in the alpha granules of circulating platelets and is known to be a mitogen and a chemotactic agent for connective tissue cells such as fibroblasts and smooth muscle cells. Because of the activities of this molecule, PDGF is believed to be a major factor involved in the normal healing of wounds and pathologically contributing to such conditions as atherosclerosis and fibrotic conditions. PDGF is a dimeric molecule consisting of combinations of α and/or β chains. The chains form heterodimers or homodimers and all combinations isolated to date are biologically active.

Studies on the role of various growth factors in tissue regeneration and repair have led to the discovery of PDGF-like proteins. These proteins share both immunological and biological activities with PDGF and can be blocked with antibodies specific to PDGF.

Polypeptide growth factors and cytokines are emerging as an important class of uterine proteins that may form growth signaling pathways between the maternal uterus and developing embryo or fetus. Studies in a variety of species have suggested that EGF, heparin-binding EGF-like growth factor (HB-EGF), IGF-I, IGF-II, aFGF, bFGF, pleitrophin (PTN), leukemia inhibitory factor, colony-stimulating factor-1 (CSF-1), and TGF-α may be among the uterine growth-regulatory molecules involved in these processes.

CTGF is a cysteine-rich monomeric peptide of $M_r$ 38,000, which is a growth factor having mitogenic and chemotactic activities for connective tissue cells. CTGF is secreted by cells and is active upon interaction with a specific cell-surface receptor. CTGF is the product of a gene unrelated to the α or β chain genes of PDGF. It is a member of a family of growth regulators which includes the mouse (also know as fisp-12 or βIG-M2) and human CTGF, Cyr61 (mouse), Cef10 (chicken), and Nov (chicken). Based on sequence comparisons, it has been suggested that the members of this family all have a modular structure, consisting of (1) an insulin-like growth factor domain responsible for binding, (2) a von Willebrand factor domain responsible for complex formation, (3) a thrombospondin type I repeat, possibly responsible for binding matrix molecules, and (4) a C-terminal module found in matrix proteins, postulated to be responsible for receptor binding.

The sequence of the cDNA for human CTGF (hCTGF) contains an open reading frame of 1047 nucleotides with an initiation site at position 130 and a TGA termination site at position 1177 and encodes a peptide of 349 amino acids. There is only a 40% sequence homology between the CTGF cDNA and the cDNA for either the α or β chains of PDGF.

The hCTGF open reading frame encodes a polypeptide which contains 39 cysteine residues, indicating a protein with multiple intramolecular disulfide bonds. The amino terminus of the peptide contains a hydrophobic signal sequence indicative of a secreted protein and there are two N-linked glycosylation sites at asparagine residues 28 and 225 in the amino acid sequence. There is a 45% overall sequence homology between the CTGF polypeptide and the polypeptide encoded by the CEF-10 mRNA transcript; the homology reaches 52% when a putative alternative splicing region is deleted.

CTGF is antigenically related to PDGF although there is little if any peptide sequence homology. Anti-PDGF antibody has high affinity to the non-reduced forms of PDGF or CTGF, and ten-fold less affinity to the reduced forms of these peptides, which lack biological activity. This suggests that there are regions of shared tertiary structure between the PDGF isomers and the CTGF molecule, resulting in common antigenic epitopes.

The synthesis and secretion of CTGF are selectively induced by TGF-β, BMP-2 and possibly other members of the TGF-β superfamily of proteins. Although TGF-β can stimulate the growth of normal fibroblasts in soft agar, CTGF alone cannot induce this property in fibroblasts. However, it has been shown that the synthesis and action of CTGF are essential for the TGF-β to stimulate anchorage independent fibroblast growth.

It is probable that CTGF functions as a growth factor in wound healing. Pathologically, CTGF has been postulated to be involved in conditions in which there is an overgrowth of connective tissue cells, such as systemic sclerosis, cancer, fibrotic conditions, and atherosclerosis.

The primary biological activity of CTGF polypeptide is its mitogenicity, or ability to stimulate target cells to proliferate. The ultimate result of this mitogenic activity in vivo, is the growth of targeted tissue. CTGF also possesses chemotactic activity, which is the chemically induced movement of cells as a result of interaction with particular molecules.

SUMMARY OF THE INVENTION

The present invention is based on the discovery, purification and characterization of heparin-binding growth factors (HBGFs) in uterine secretory fluids. These growth factor polypeptides bind heparin and exhibit many of the functional characteristics of full length CTGF.

In a first aspect, the present invention provides heparin-binding polypeptides (HBGF polypeptides) that have been identified as having mitogenic activity and nucleic acids encoding such polypeptides.

In yet a further aspect of the present invention, there are provided antibodies which bind to HBGFs.

In yet a further aspect of the present invention, there are also provided nucleic acid probes comprising nucleic acid molecules of sufficient length to specifically hybridize to a nucleic acid sequence encoding HBGFs.

In accordance with yet a further aspect of the invention, there is provided a method for using HBGFs, the nucleic acid molecules encoding HBGFs, or antisense sequences to nucleic acid molecules encoding HBGFs for affecting wound healing, tissue formation, sclerotic or cell proliferative disorders, atherosclerosis or fibrotic disease.

BRIEF DESCRIPTION OF THE DRAWINGS

The following drawings are illustrative of embodiments of the invention and are not meant to limit the scope of the invention as encompassed by the claims.

DETAILED DESCRIPTION OF THE PREFERRED EMBODIMENTS

Figure 1A:
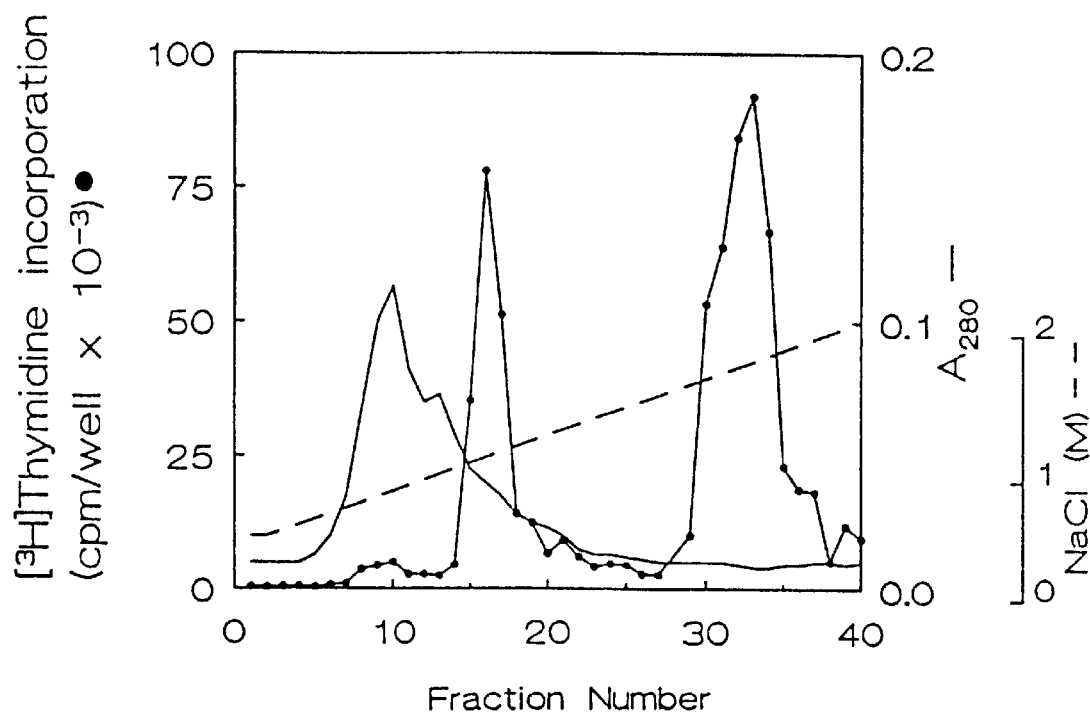
FIG. 1a is an illustration showing the results of heparin affinity chromatographic fractions of uterine luminal flushings that were assayed for stimulation of DNA synthesis.
Figure 1B:
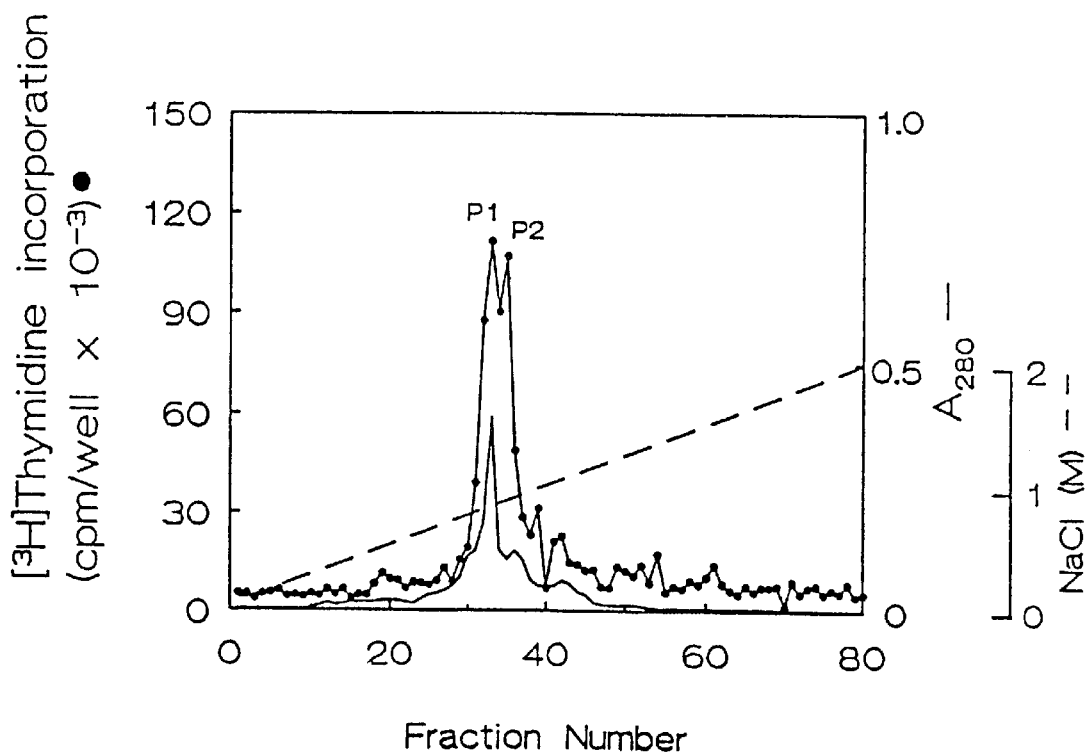
FIG. 1b is an illustration showing the results of subsequent heparin affinity chromatography on samples positive for DNA synthesis (from FIG. 1a) in which the principal component peaks (labeled P1 and P2) represent the HBGF-0.8 polypeptides.
Figure 2:
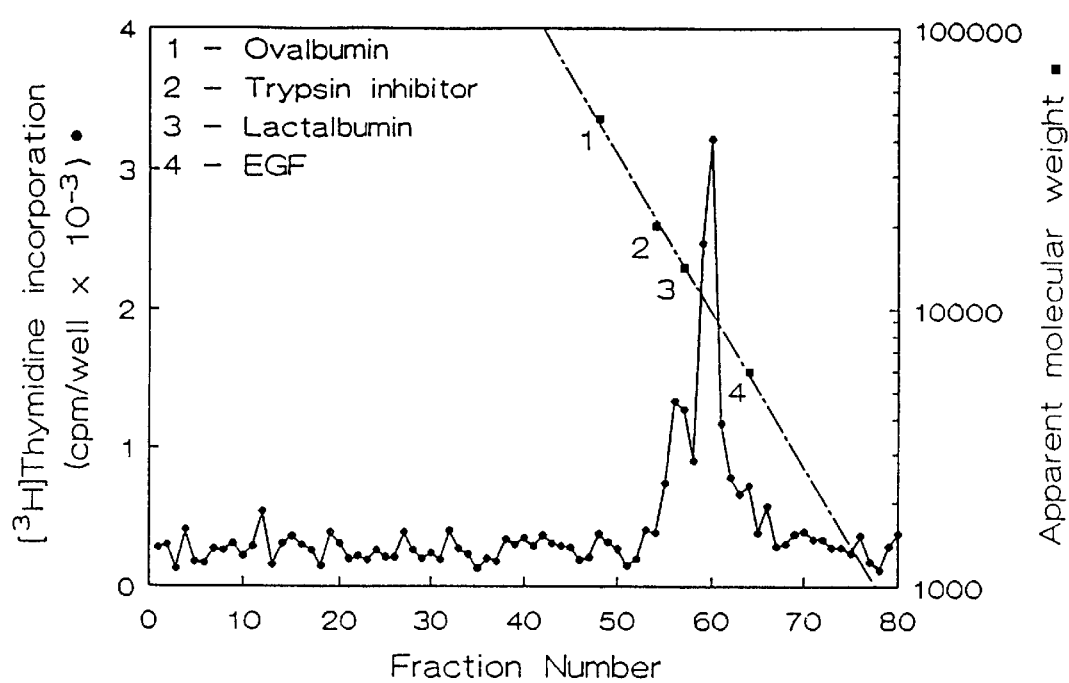
FIG. 2 is an illustration showing a gel filtration chromatography profile of the HBGF-0.8 polypeptides.
Figure 3A:
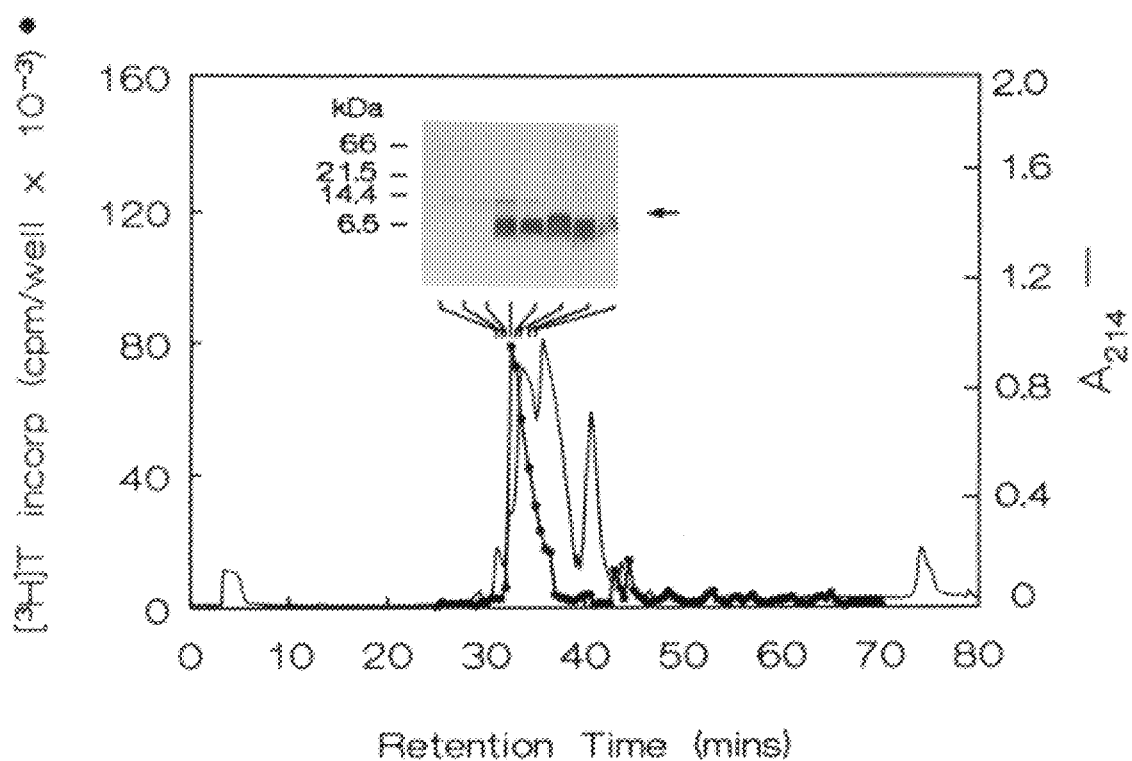
FIGS. 3A and 3B show the reverse-phase HPLC and SDS-PAGE of the HBGF-0.8 polypeptides.
Figure 3B:
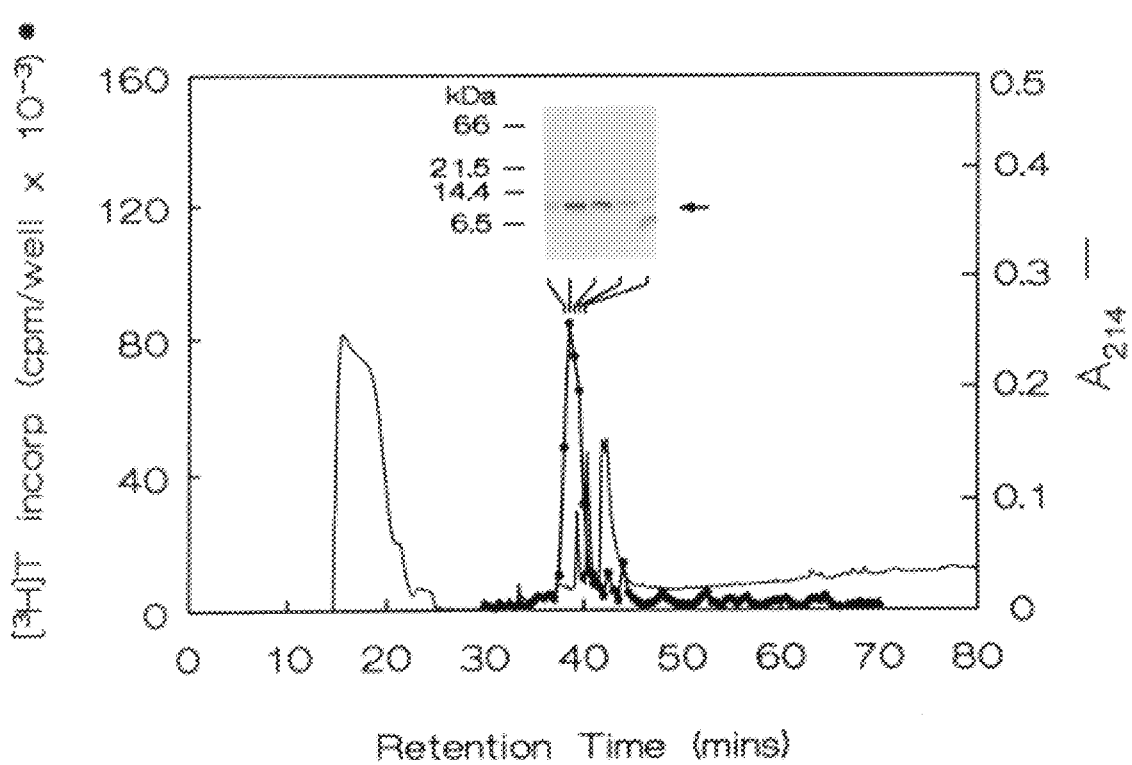
Figure 4:
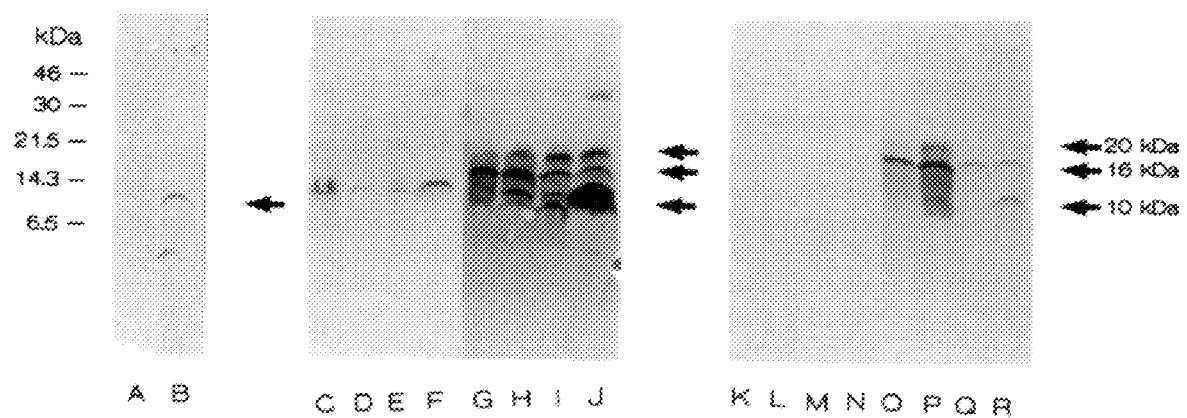
FIG. 4 is an illustration showing a Western blot analysis of unpurified uterine luminal flushings.
Figure 5:
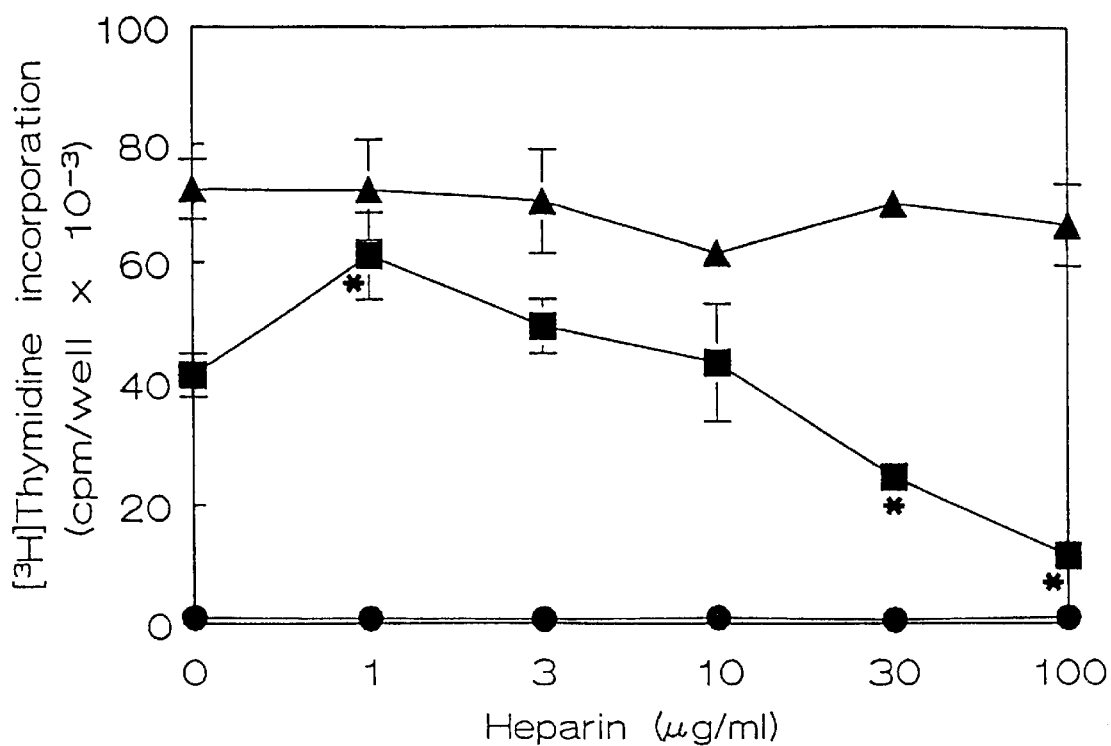
FIG. 5 is an illustration showing the effect of mitogenic activity of the HBGF-0.8 polypeptides.
Figure 6:
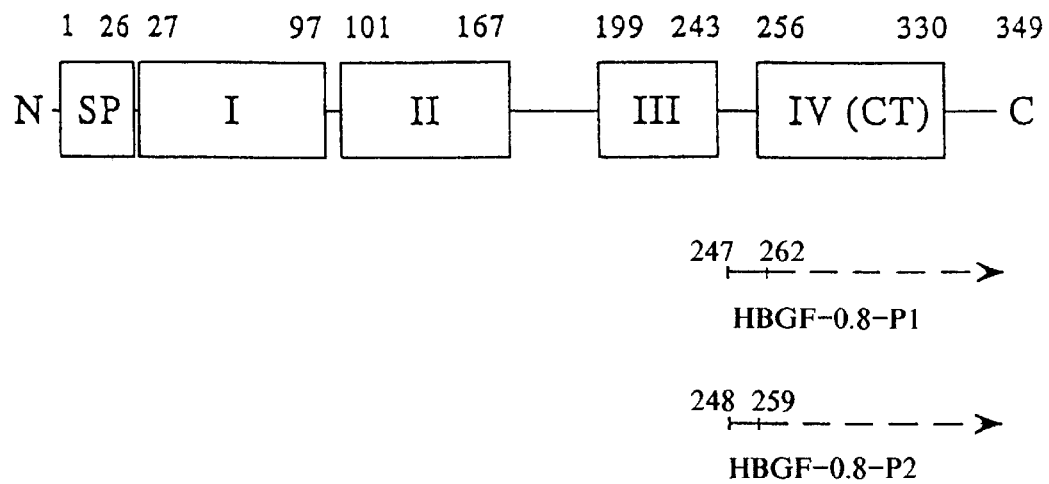
FIG. 6 is an illustration showing the relationship between the HBGF-0.8 polypeptides and the CTGF primary translational product.

Before the present methods, apparatus, compositions and formulations are described, it is to be understood that this invention is not limited to the particular methods, apparatus, compositions and formulations described herein, as such methods, apparatus, compositions and formulations may, of course, vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a," "an," and "the" include plural referents unless the context clearly dictates otherwise. Thus, for example, reference to "an organism" includes one or more different organisms, reference to "an amino acid" includes one or more of such amino acids, and reference to "a method" include reference to equivalent steps and methods known to those skilled in the art, and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described. The publications discussed above are provided solely for their disclosure prior to the filing date of the present application. Nothing herein is to be construed as an admission that the invention is not entitled to antedate such disclosure by virtue of prior invention.

The present invention provides heparin-binding growth factors (HBGF polypeptides or HBGFs), which are mitogenic for fibroblasts and smooth muscle cells in vitro. HBGFs are heat- and acid-labile, and exist in two forms, HBGF-0.8-P1, and HBGF-0.8-P2, each of which has different heparin binding properties, and each of which has a $M_r$ of about 10-kDa under reducing conditions by SDS-PAGE. HBGFs are related structurally and functionally to CTGF.

Both HBGF-0.8-P1 and HBGF-0.8-P2 require the presence of 0.8M NaCl for elution from a heparin affinity column. Sequencing revealed that the N-terminal sequence of HBGF-0.8-P1 corresponded to amino acid residues 247–262 of the 349-residue predicted primary translation product of porcine connective tissue growth factor (CTGF) while the N-terminal sequence of HBGF-0.8-P2 corresponded to amino acid residues 248–259 of CTGF. Thus, HBGFs correspond to two microheterogenous, highly truncated N-terminal forms of the translation product of CTGF, both of which are biologically active. HBGF-0.8-P2 is identical to HBGF-0.8-P1 except for the presence of an additional Glu residue at the N-terminus of HBGF-0.8-P1.

The HBGFs of the invention are highly N-terminally truncated forms of CTGF, however, there is no intron/exon boundary that could directly give rise to the N terminus of the two proteins. HBGFs do not align with the proposed modular components of CTGF; the proteins of the invention contain none of the sulfated glycoconjugate binding motif of CTGF, termed a thrombospondin type I repeat, which is postulated to be responsible for binding matrix molecules. A C-terminal module of CTGF found in matrix proteins, which is postulated to be involved in receptor binding, is entirely present in the HBGFs. The proposed binding motif for sulfated glycoconjugates between amino acid residues 206 and 214 of CTGF is absent from HBGFs, yet HBGFs bind heparin, and the heparin interactions are functionally significant. The N terminus of HBGF-0.8-P1 and HBGF-0.8-P2 may be involved in heparin binding, as the two proteins of the invention differ by only a single N-terminal Glu, yet display differential binding to heparin.

The HBGFs of the invention are secreted from both cultured human and mouse fibroblasts. Production of HBGFs is not limited to a particular species or biological system. Preferably, the HBGFs of the invention are mitogenic and chemotactic for mesenchymally derived cells (e.g., fibroblasts, chondrocytes, osteoclasts, osteoblasts, and astroglial), however, other cell types (e.g., muscle cells, connective tissue cells, epithelial cells and secretory cells) are responsive to HBGFs as well. HBGFs can play a significant role in the normal development, growth and repair of human tissue. HBGFs are present in uterine flushings, and may play an additional role in the growth and remodeling of the endometrium, and, during pregnancy, may affect the growth and development of the extra-embryonic or placental membranes.

Therapeutic agents derived from HBGFs can be useful in augmenting normal or impaired growth processes involving connective tissues in certain clinical states (e.g., wound healing). When these HBGFs are involved in pathological conditions, therapeutic developments from these proteins can be used to control or modulate uncontrolled tissue growth.

The term "substantially pure" as used herein refers to HBGFs which are substantially free of other proteins, lipids, carbohydrates or other materials with which they are naturally associated. A substantially pure HBGF polypeptide will yield a single major band on a non-reducing polyacrylamide gel. The purity of HBGFs can also be determined by amino-terminal amino acid sequence analysis. HBGFs, as defined herein, include functional fragments of the polypeptide, so long as HBGF biological activity is retained (e.g., inducing a biologic response in fibroblasts as determined using standard assays common in the art and as taught herein). Smaller polypeptides containing HBGF biological activity are included in the invention. Additionally, more effective HBGFs produced, for example, through site directed mutagenesis of HBGF polypeptide cDNA are included. "Recombinant" HBGFs refer to HBGF polypeptides produced by recombinant DNA techniques; i.e., produced from cells transformed by an exogenous DNA construct encoding the desired HBGF polypeptide. "Synthetic" HBGFs are those prepared by chemical synthesis. A DNA "coding sequence of" or a "nucleotide sequence encoding" a particular HBGF polypeptide, is a DNA sequence which is transcribed and translated into an HBGF polypeptide when placed under the control of appropriate regulatory sequences.

The invention provides nucleic acids encoding HBGF polypeptides. These nucleic acids include DNA, cDNA and RNA sequences which encode for HBGFs. It is understood that all nucleic acids encoding all or a portion of HBGF polypeptides are also included herein, so long as they encode a polypeptide with HBGF biological activity. Such nucleic acids include both naturally occurring and intentionally manipulated nucleic acids. For example, HBGF polypeptides may be subjected to site-directed mutagenesis.

The nucleic acids of the invention include sequences that are degenerate as a result of the genetic code. There are only 20 natural amino acids, most of which are specified by more than one codon. Therefore, as long as the amino acid sequence of an HBGF polypeptide is functionally unchanged, all degenerate nucleotide sequences are included in the invention. The fragment, derivative or analog of the HBGF polypeptides may be (i) one in which one or more of the amino acid residues are substituted with a conserved or non-conserved amino acid residue (preferably a conserved amino acid residue) and such substituted amino acid residue may or may not be one encoded by the genetic code, or among preferred variants are those that vary from a reference by conservative amino acid substitutions, (such substitutions are those that substitute a given amino acid in a polypeptide by another amino acid of like characteristics. Typically, conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr); (ii) one in which one or more of the amino acid residues includes a substituent group; (iii) one in which an HBGF polypeptide is fused with another compound, such as a compound to increase the half-life of the HBGF polypeptides (for example, polyethylene glycol); or (iv) one in which additional amino acids are fused to HBGF polypeptides, such as a leader or secretory sequence or a sequence which is employed for purification of HBGF polypeptides or a pro-protein sequence. Such fragments, derivatives and analogs are deemed to be within the scope of those skilled in the art from the teachings herein. The HBGFs of the present invention and nucleic acids coding for them are preferably provided in an isolated form, and preferably are purified to homogeneity.

DNA sequences encoding the HBGF polypeptides of the invention can be obtained by several methods. For example, the DNA can be isolated using well known hybridization procedures. These include, but are not limited to: 1) hybridization of probes to genomic or cDNA libraries to detect shared nucleotide sequences (see, for example: *Current Protocols in Molecular Biology,* Ausubel F. M. et al. (EDS.) Green Publishing Company Assoc. and John Wiley Interscience, New York, Current Edition) and 2) antibody screening of expression libraries to detect shared structural features. It is appreciated by one skilled in the art that the nucleic acids (comprising at least 12 contiguous nucleotides) encoding the HBGFs, are particularly useful as probes.

"Selective hybridization" as used herein refers to hybridization under moderately stringent or highly stringent physiological conditions (See, J. Sambrook et al., *Molecular Cloning, A Laboratory Manual,* Cold Spring Harbor Laboratory (Current Edition) which is hereby incorporated by reference in its entirety) that distinguish related from unrelated HBGF based upon the degree of identity between nucleotide sequences in proximity for hybridization to occur. Also, it is understood that a fragment of a 100 bps sequence that is 95 bps in length has 95% identity with the 100 bps sequence from which it is obtained. As used herein, a first DNA (RNA) sequence is at least 70% and preferably at least 80% identical to another DNA (RNA) sequence if there is at least 70% and preferably at least a 80% or 90% identity, respectively, between the bases of the first sequence and the bases of another sequence, when properly aligned with each other, for example, when aligned by BLASTN.

"Identity" as the term is used herein, refers to a polynucleotide sequence which comprises a percentage of the same bases as a reference polynucleotide. For example, a polynucleotide which is at least 90% identical to a reference polynucleotide, has polynucleotide bases that are identical in 90% of the bases which make up the reference polynucleotide (i.e., when the sequences are properly aligned with each other using standard alignment and homology adjustments common to those in the art (e.g., NetBlast or GRAIL)) and may have different bases in 10% of the bases which comprise that polynucleotide sequence.

Screening procedures which rely on nucleic acid hybridization make it possible to isolate any gene sequence from any organism, provided the appropriate probe is available. For example, oligonucleotide probes, which correspond to a part of the sequence encoding the protein in question, can be synthesized chemically. This requires that short, oligopeptide stretches of amino acid sequence must be known. The DNA sequence encoding the protein can be deduced from the genetic code, however, the degeneracy of the code must be taken into account. It is possible to perform a mixed addition reaction when the sequence is degenerate. This includes a heterogeneous mixture of denatured double-stranded DNA. For such screening, hybridization is preferably performed on either single-stranded DNA or denatured double-stranded DNA. Hybridization is particularly useful in the detection of cDNA clones derived from sources where an extremely low amount of mRNA sequences relating to the polypeptide of interest is present. In other words, by using selective hybridization conditions directed to avoid non-specific binding, it is possible, for example, to allow the autoradiographic visualization of a specific cDNA clone by the hybridization of the target DNA to that single probe in the mixture which is its complete complement (Wallace, et al, *Nucleic Acid Research,* 9:879, 1981). It is also appreciated that such selective hybridization probes can be and are preferably labeled with an analytically detectable reagent to facilitate identification of the probe. Useful reagents include but are not limited to radioactivity, fluorescent dyes or enzymes capable of catalyzing the formation of a detectable product. The selective hybridization probes are thus useful to isolate complementary copies of DNA from other sources or to screen such sources for related sequences.

A cDNA expression library, such as lambda gt11, can be screened indirectly for HBGFs having at least one epitope, using antibodies specific for HBGF polypeptides or antibodies to CTGF which cross react with HBGF polypeptides, or antibodies to PDGF which cross react with HBGF polypeptides. Such antibodies can be either polyclonally or monoclonally derived and used to detect expression products indicative of the presence of HBGF polypeptide cDNA.

DNA sequences encoding HBGF polypeptides can be expressed in vitro by DNA transfer into a suitable host cell. "Host cells" are genetically engineered cells (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the genes of the present invention. The culture conditions, such as temperature, pH and the like, are those previously used with the host cell selected for expression, and will be apparent to the ordinarily skilled artisan. The term also includes any progeny of the subject host cell. It is understood that all progeny may not be identical to the parental cell since there may be mutations that occur during replication. However, such progeny are included when the term "host cell" is used. Introduction of the construct into the host cell can be effected by calcium phosphate transfection, DEAE-Dextran mediated transfection, electroporation or any other method of the art (Davis, L. et al., *Basic Methods in Molecular Biology*, (Current Edition)).

The nucleic acids of the present invention may be employed for producing HBGFs by recombinant techniques. Thus, for example, the polynucleotide may be included in any one of a variety of expression vectors for expressing HBGF polypeptides. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art. DNA sequences encoding HBGFs can be expressed in vivo in either prokaryotes or eukaryotes. Methods of expressing DNA sequences having eukaryotic coding sequences in prokaryotes are well known in the art. Hosts include microbial, yeast and mammalian organisms.

Biologically functional viral and plasmid DNA vectors capable of expression and replication in a host are known in the art. Such vectors are used to incorporate DNA sequences of the invention. In general, expression vectors containing promotor sequences which facilitate the efficient transcription of the inserted eukaryotic genetic sequence are used in connection with the host. The expression vector typically contains an origin of replication, a promoter, and a terminator, as well as specific genes capable of providing phenotypic selection of the transformed cells.

In addition to expression vectors known in the art such as bacterial, yeast and mammalian expression systems, baculovirus vectors may also be used. One advantage to expression of foreign genes in this invertebrate virus expression vector is that it is capable of expression of high levels of recombinant proteins, which are antigenically and functionally similar to their natural counterparts. Baculovirus vectors and the appropriate insect host cells used in conjunction with the vectors are known to those skilled in the art. The isolation and purification of host cell expressed polypeptides of the invention may be by any conventional means such as, for example, preparative chromatographic separations and immunological separations such as those involving the use of monoclonal or polyclonal antibodies.

The invention provides antibodies which are specifically reactive with HBGF polypeptides or fragments thereof Although this polypeptide may be cross reactive with antibodies to PDGF or CTGF, not all antibodies to HBGFs will also be reactive with PDGF, and not all antibodies to CTGF will be reactive to HBGFs. Antibody which consists essentially of pooled monoclonal antibodies with different epitopic specificities, as well as distinct monoclonal antibody preparations are provided. Monoclonal antibodies are made from antigen containing fragments of the protein by methods well known in the art (Kohler, et al., *Nature* 256:495, 1975; *Current Protocols in Molecular Biology*, Ausubel, et al., ed., 1989). Polyclonal antibodies to the HBGFs of the invention are also included using methods common to those in the art (see Harlow and Lane, 1988, *Antibodies, A Laboratory Manual*, Cold Spring Harbor Laboratory, New York, Current Edition). Monoclonal antibodies specific for HBGFs can be selected, for example, by screening for hybridoma culture supernatants which react with HBGF polypeptides, but do not react with PDGF. Antibodies generated against HBGFs corresponding to the present invention can be obtained by direct injection of the polypeptides into an animal or by administering the polypeptides to an animal, preferably a nonhuman. The antibody so obtained will then bind the polypeptide itself. In this manner, even a sequence encoding only a fragment of the polypeptides can be used to generate antibodies binding the original polypeptides. Such antibodies can then be used to isolate the polypeptides from cells expressing that polypeptide.

For preparation of monoclonal antibodies, any technique which provides antibodies produced by continuous cell line cultures can be used. Examples include the hybridoma technique (Kohler, et al., *Nature* 256:495, 1975), the trioma technique, the human B-cell hybridoma technique (Kozbor et al., 1983, *Immunology Today* 4:72), and the EBV-hybridoma technique to produce human monoclonal antibodies (Cole, et al., 1985, in *Monoclonal Antibodies and Cancer Therapy*, Alan R. Liss, Inc., pp. 77–96).

Techniques described for the production of single chain antibodies (U.S. Pat. No. 4,946,778) can be adapted to produce single chain antibodies to immunogenic peptide products of this invention. Additionally included within the bounds of the invention, are the production and use for diagnostic and therapeutic applications of both "human" and "humanized" antibodies directed to HBGF polypeptides or fragments thereof. Humanized antibodies are antibodies, or antibody fragments, that have the same binding specificity as a parent antibody (i.e., typically of mouse origin), but which have increased human characteristics. Humanized antibodies may be obtained by chain shuffling, or using phage display technology. For example, a polypeptide comprising a heavy or light chain variable domain of a non-human antibody specific for a HBGF is combined with a repertoire of human complementary (light or heavy) chain variable domains. Hybrid pairings which are specific for the antigen of interest are selected. Human chains from the selected pairings may then be combined with a repertoire of human complementary variable domains (heavy or light) and humanized antibody polypeptide dimers can then be selected for binding specificity for an antigen. Such techniques are described in U.S. Pat. No. 5,565,332 or can be obtained commercially (Scotgene, Scotland or Oxford Molecular, Palo Alto, Calif., USA). Furthermore, techniques described for the production of "human" antibodies (i.e., de novo antibodies with human constant region sequences) in transgenic mice (U.S. Pat. No. 5,545,806 and U.S. Pat. No. 5,569,825) can also be adapted to produce "human" HBGF antibodies or antibody fragments or may also be commercially contracted (GenPharm International, Inc., Mountain View, Calif., USA).

Antibodies generated against the polypeptides of the present invention may be used in screening for similar HBGF polypeptides from other organisms and samples. Such screening techniques are known in the art.

The invention provides a method for accelerating wound healing in a subject, e.g., human, by applying to the wound an therapeutically effective amount of a composition which contains purified HBGF polypeptides, PDGF, PDGF-related molecule or combinations thereof. The HBGF polypeptides of this invention are valuable as a therapeutic in cases in which there is impaired healing of skin wounds or there is a need to augment normal healing mechanisms. HBGF polypeptides, or functional fragments thereof, are more stable and less susceptible to protease degradation than PDGF and other growth factors known to be involved in wound healing. In addition, HBGF polypeptides may have a higher specific biologic activity than CTGF.

HBGF polypeptides are derived from fibroblastic cells, which are present at a wound site. Therefore, agents which stimulate the production of HBGF polypeptides can be added to a composition that is used to accelerate wound healing. Preferably, the agent is a member of the family of growth factors such as insulin-like growth factor (IGF-I), platlet-derived growth factor (PGF), epidermal growth factor (EGF), transforming growth factor beta (TGF-$\beta$) and basic fibroblast growth factor (bFGF). More preferably, the agent is transforming growth factor beta (TGF-$\beta$) or other member of the TGF-$\beta$ superfamily. Additionally, the biologic effect of HBGF can be modulated by the addition of heparin in a concentration in the range of about 1 $\mu$g/ml to 100 $\mu$g/ml. The HBGF compositions of the invention aid in healing the wound, in part, by promoting the growth of connective tissue. The HBGF compositions are prepared by combining, in any pharmaceutically acceptable carrier substance, e.g., inert gels or liquids, the purified HBGF polypeptides of the invention. Other modulating compositions such as heparin, or growth factors such as TGF-$\beta$ can be included in the HBGF compositions.

The term "cell proliferative disorder" refers to a condition characterized by an abnormal number of cells. The condition can include both hypertrophic (the continual multiplication of cells resulting in an overgrowth of a cell population within a tissue) and hypotrophic (a lack or deficiency of cells within a tissue) cell growth or an excessive influx or migration of cells into an area of a body. The cell populations are not necessarily transformed, tumorigenic or malignant cells, but can include normal cells as well. For example, HBGFs may be involved in a pathological condition by inducing a proliferative lesion in the intimal layer of an arterial wall, resulting in atherosclerosis. Instead of trying to reduce risk factors for the condition, e.g., lowering blood pressure or reducing elevated cholesterol levels, HBGF polypeptide inhibitors or antagonists of the invention would be useful in interfering with the in vivo activity of HBGFs associated with atherosclerosis. HBGF polypeptide antagonists are also useful in treating other disorders associated with an overgrowth of connective tissues, such as various fibrotic conditions, including scleroderma, arthritis and liver cirrhosis.

These diseases, disorders or ailments modulated by HBGF include tissue repair subsequent to traumatic injuries or conditions including arthritis, osteoporosis and other skeletal disorders, and burns. Because these problems are due to a poor growth response of the fibroblasts, stem cells, chondrocytes, osteoblasts or fibroblasts at the site of injury, the addition of an active biologic agent that stimulates or induces growth of these cells is beneficial. The term "induce" or "induction" as used herein, refers to the activation, stimulation, enhancement, initiation and or maintenance of the cellular mechanisms or processes necessary for the formation of any of the tissue, repair process or development as described herein The present invention further provides a method for modulating female reproductive tract function. Growth factors have been shown to play a role in cyclic mitosis and differentiation of endometrial cellular components, recruitment of macrophages in decidualizing the endometrium, endometrial-trophoblast interactions, early pregnancy maintenance, and endometrial functional regeneration. The term "modulate" as used herein, denotes a modification of an existing condition or biologic state. Modulation of a condition as defined herein, encompasses both an increase or a decrease in the determinants affecting the existing condition. For example, administration of HBGFs could be used to augment uterine functions in a condition where the promotion of growth is desired. For example, the uterus may be treated with HBGFs to promote the growth and development of placental membranes or endometrial growth. Furthermore, treatment with HBGFs may be used to promote and maintain a pregnancy by facilitating endometrial-trophoblast interaction. Alternatively, antagonists to HBGFs are administered to modulate conditions of excessive endometrial growth in which the level of HBGF is excessive in comparison to a normal biologic condition.

The invention also discloses a method for treating conditions characterized by a cell proliferative disorder by treating the condition using an therapeutically effective amount of a HBGF reactive agent. The term "treat" denotes a lessening of the detrimental effect of the condition in the subject receiving the reactive agent. Where the condition is due to an overgrowth of cells, an antagonist of HBGF is therapeutically effective in decreasing the amount of growth factor that can bind to an HBGF specific receptor on a cell. Such an antagonist may be a HBGF specific antibody or functional fragments thereof (e.g., Fab, F(ab)). The treatment requires contacting or delivering to the site of the condition with the antagonist of the HBGF polypeptide. Where the cell proliferative disorder is due to a diminished amount of growth of cells, a HBGF reactive agent which is stimulatory is contacted with, or delivered to the site of the condition. For example, TGF-$\beta$ (or another member of the TGF-$\beta$ superfamily) can be such a reactive agent. Other biologic agents will be known to those skilled in the art.

When a cell proliferative disorder is associated with the expression of HBGFs, a therapeutic approach which directly interferes with the transcription of HBGF into mRNA or the translation of HBGF mRNA into protein is possible. For example, antisense nucleic acid or ribozymes that bind to the HBGF mRNA or cleave it are also included within the invention. Antisense RNA or DNA molecules bind specifically with a targeted gene's RNA message, interrupting the expression of that gene's protein product. The antisense binds to the mRNA forming a double stranded molecule which cannot be translated by the cell. Antisense oligonucleotides of about 15–25 nucleotides are preferred since they are easily synthesized and have an inhibitory effect just like antisense RNA molecules. In addition, chemically reactive groups, such as iron-linked ethylenediaminetetraacetic acid (EDTA-F$_c$) can be attached to an antisense oligonucleotide, causing cleavage of the RNA at the site of hybridization. These and other uses of antisense methods to inhibit the in vivo translation of genes are well known in the art (e.g., De Mesmaeker, et al., 1995. Backbone modifications in oligonucleotides and peptide nucleic acid systems. *Curr. Opin. Struct. Biol.* 5:343–355; Gewirtz, A. M., et al., 1996b. Facilitating delivery of antisense oligodeoxynucleotides: Helping antisense deliver on its promise; *Proc. Natl. Acad. Sci. U.S.A.* 93:3161–3163; Stein, C. A. A discussion of G-tetrads 1996. Exploiting the potential of antisense: beyond phosphorothioate oligodeoxynucleotides. *Chem. and Biol.* 3:319–323).

Another therapeutic approach included within the invention involves direct administration of reagents or compositions including the HBGFs of the invention by any conventional administration technique (for example, but not restricted to, local injection, inhalation, or systemic administration), to a subject with a fibrotic, a scelortic, or a cell proliferative disorder, atherosclerosis. Administration of HBGFs, as described above, accelerate wound healing, can induce the formation of tissue repair or regeneration, or the growth and development of the endometrium. The reagent, formulation or composition may also be targeted to specific cells or receptors by any method described herein or by any method known in the art of delivering, targeting and expressing genes encoding HBFG. The actual dosage of reagent, formulation or composition that modulates a fibrotic disorder, a scelortic disorder, a cell proliferative disorder, atherosclerosis or wound healing depends on many factors, including the size and health of an organism. However, one of ordinary skill in the art can use the following teachings describing the methods and techniques for determining clinical dosages (Spilker B., *Guide to Clinical Studies and Developing Protocols,* Raven Press Books, Ltd., New York, 1984, pp. 7–13, 54–60; Spilker B., *Guide to Clinical Trials,* Raven Press, Ltd., New York, 1991, pp. 93–101; Craig C., and R. Stitzel, eds., *Modern Pharmacology,* 2d ed., Little, Brown and Co., Boston, 1986, pp. 127–33; T. Speight, ed., *Avery's Drug Treatment: Principles and Practice of Clinical Pharmacology and Therapeutics,* 3d ed., Williams and Wilkins, Baltimore, 1987, pp. 50–56; R. Tallarida, R. Raffa and P. McGonigle, *Principles in General Pharmacology,* Springer-Verlag, New York, 1988, pp. 18–20) or to determine the appropriate dosage to use; but, generally, in the range of about between 0.5 µg/ml and 500 µg/ml inclusive final concentration are administered per day to an adult in any pharmaceutically-acceptable carrier.

The present invention also provides a method to detect the presence of abnormal levels of HBGFs in a subject to be used diagnostically to determine the presence of conditions or pathologies associated with abnormal levels of HBGFs. Such conditions include but are not restricted to cell proliferative disorders, various fibrotic conditions including scleroderma, arthritis, liver cirrhosis, and uterine fibroids. For example, a sample suspected of containing HBGFs is obtained from a subject, the level of HBGF polypeptide is determined and compared with the level of HBGF polypeptide in a normal tissue sample. The level of HBGFs can be determined by immunoassays using anti-HBGF polypeptide antibodies, for example. Other variations of such assays include radioimmunoassay (RIA), ELISA and immunofluorescence. Alternatively, nucleic acid probes can be used to detect and quantitate HBGF polypeptide mRNA for the same purpose.

The following examples are put forth so as to provide those of ordinary skill in the art with a complete disclosure and description of how to make and use the HBGFs of the present invention, and are not intended, nor should they be construed, to limit the scope of what the inventors regard as their invention. Efforts have been made to ensure accuracy with respect to numbers used (e.g., amounts, time, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

EXAMPLE 1

Characterization and Purification of HBGF Polypeptides

Uteri were collected at random from slaughterhouse pigs that were approximately 8 months or less in age. Each uterine horn was flushed with cold (4° C.) phosphate-buffered saline (PBS) to collect uterine luminal components. Growth factor purification was performed on 4-liter pools of ULF obtained from up to 120 animals. Uterine luminal flushings (ULF) were clarified by centrifugation at 13,500×g for 30 minutes at 4° C., and the supernatant was passed through glass wool.

Four liter samples of clarified ULF supernatant were applied at 4° C. to a BioRex 70 cation exchange column (5×6 cm; Bio-Rad) that had previously been equilibrated in PBS, 0.2M NaCl. After sample application, the column was washed with 500 ml of PBS, 0.2M NaCl, and bound proteins were eluted using a 500 ml gradient of 0.2–2M NaCl in PBS. The flow rate was 3.5 ml/min throughout, and fractions of 10 ml were collected during treatment of the column with the NaCl gradient. Fractions demonstrating mitogenic activity for Balb/c 3T3 fibroblasts were selected for further use. All subsequent chromatographic steps were performed at room temperature.

The ion exchange chromatograph of ULF showed the presence of cationic growth factor activity for Balb/c 3T3 cells eluted from BioRex 70 columns by 0.3–0.6M NaCl. Heparin affinity chromatography revealed the presence of an additional unidentified HBGF polypeptide that required 0.8M NaCl for elution from an EconoPac heparin column. In terms of the amount of bioactivity recovered from the column, the fraction requiring 0.8M NaCl for elution appeared to be a principal cationic heparin-binding growth factor for 3T3 cells. The elution position of HBGF polypeptides from heparin affinity columns was clearly distinct from PDGF, HB-EGF, PTN, aFGF, bFGF, and amphiregulin. HBGF mitogenic activity was destroyed by exposure to heat (100° C. for 2 mins or 56° C. for 30 mins) or acid (pH2.0 for 2 mins).

Gel filtration chromatography was used to show that HBGFs had an apparent relative molecular mass of approximately 10,000 daltons. For these studies, 0.5 ml of a fraction containing the 0.8M NaCl eluate from EconoPac heparin affinity FPLC of ULF from 30 animals was applied at 0.5 ml/min to a TSK G2000 SW FPLC column (30 cm×8 mm, 10-µm particle size, M, 500–100,000 fractionation range; TosoHaas) equipped with a SW guard column (4 cm×8 mm, 10-µm; TosoHaas). Proteins were eluted with PBS containing 0.3M NaCl. Fractions of 200 µl were collected and tested for their ability to stimulate DNA synthesis in 3T3 cells. Column calibration was performed using EGF (6,000 MW), lactalbumin (14,200 MW), trypsin inhibitor (20,100 MW), and ovalbumin (45,000 MW). Fractions were tested for their ability to stimulate DNA synthesis in 3T3 cells at 40 μl/ml, as described above.

Fractions that contained HBGF activity (fractions 16–19 collected after the cation exchange chromatography and heparin affinity chromatography) were pooled, diluted, and subjected to a second cycle of heparin affinity FPLC using a TSK heparin 5PW column. To perform the second heparin affinity purification step, biologically active HBGF fractions containing the 0.8M NaCl eluate from the EconoPac heparin purification step were pooled, diluted 3-fold with 20 mM Tris-HCl (pH 7.4), and clarified by passage through a 0.2-μm filter. The sample was applied at 2 ml/min to a TSK heparin 5PW column (0.8×7.5 cm; TosoHaas, Philadelphia, Pa.), that was washed and eluted as described above, except that CHAPS was omitted from the buffers and fractions of 0.5 ml were collected. Fractions containing proteins that were eluted by 0.8M NaCl and which demonstrated mitogenic activity of 3T3 cells were divided into two pools consisting of fractions 31–34 (peak 1) and fractions 35 and 36 (peak 2). HBGF polypeptide was again eluted by 0.8M NaCl (fractions 31–36), but was resolved as two peaks of mitogenic activity which had distinct heparin binding properties. The activity peaks were termed HGBF-0.8-P1 for fractions 31–34 and HGBF-0.8-P2 for fractions 35 and 36.

HBGF-0.8-P1 and -P2 were adjusted to 10% acetonitrile, 0.1% trifluroacetic acid, and individually subjected to $C_8$ reverse-phase HPLC. Reverse-phase HPLC was performed on a Hitachi HPLC system (Hitachi Instruments Inc., Danbury, Conn.) using a $C_8$ column (0.46×25 cm, 5-μm particle size; Rainin Instrument Co., Woburn, Mass.) that was equilibrated with water containing 10% (v/v) acetonitrile and 0.1% (v/v) trifluoroacetic acid. Pooled fractions containing peaks 1 and 2 from the TSK heparin purification step were individually adjusted so that they contained 10% acetonitrile, 0.1% trifluoroacetic acid and were clarified by passage through a 0.2-μm filter. Conditions for the elution of bound proteins were 10% acetonitrile from zero to 10 min. after sample injection and 10–90% from 10 min. to 146 min. The flow rate was 1 ml/min throughout, and the chromatogram ($A_{214}$) was archived as described (Bray, and Brigstock, (1994) *Amer. Lab.* 26, 38). The eluate was collected as 0.5 ml fractions in siliconized tubes containing 50 μl of 125 mM NaOH to immediately neutralize the trifluoroacetic acid. The 80 μl aliquots of selected fractions were evaporated to dryness in a SpeedVac concentrator (Savant Instruments, Farmingdale, N.Y.) and reconstituted in 25 μl of 10 mM Tris-HCl (pH 7.4). 10 μl of this concentrate were assayed for their stimulation of 3T3 cell DNA synthesis, and 10 μl were used for analytical SDS-PAGE. For the second step $C_8$ HPLC purification, two active fractions from the first HPLC step were pooled (1 ml total volume), diluted 5-fold with water, 0.1% trifluoroacetic acid, and subjected to the same chromatographic elution conditions as described herein. The elution positions of HGBF-0.8-P1 and -P2 were determined by bioassay of aliquots of fractions containing the column eluate after they had been evaporated and reconstituted in PBS, demonstrating that there was sufficient activity in the purified HGBF samples to permit their detection and further characterization despite prolonged (approximately 30 to 40 minute) exposure to pH=2 during the HPLC step.

Following HPLC, silver-stained SDS-PAGE analysis of the fractions containing either HBGF-0.8-P1 or -P2 was performed under reducing conditions using 18% polyacrylamide mini-gels as described (Kim, G. Y., et al., (1995) *Biol. Reprod.* 52, 561–571). Subsequently, silver staining of proteins was performed as described (Wray, W., et al., (1981) *Anal Biochem.* 118, 197–203). SDS-PAGE was performed on (i) HPLC-purified growth factors, (ii) 8 μl of unfractionated ULF, or (iii) 100 μl of ULF after passage through 20-μl beds of heparin-Sepharose in the presence of 10 mM Tris-HCl, 0.5M NaCl (pH 7.4) and subsequent extraction of the heparin beads with SDS-PAGE sample buffer. Gels were then prepared as described (Kim, G. Y., et al., (1995) *Biol. Reprod.* 52, 561–571). Subsequent analysis revealed the presence of a single 10-kDa protein that co-purified with Balb/c 3T3 mitogenic activity. Levels of mitogenic activity were directly correlated with those of the 10-kDa protein, which was completely pure as shown by silver staining. The results from 18 individual HPLC purifications confirmed a direct, causative relationship between the 10-kDa protein(s) and the mitogenic activity of HBGF-0.8-P1 and -P2.

Analysis of the individual purification steps showed that 0.5–1.1 μg of HBGF-0.8-P1 or -P2 were each purified from 342 mg of crude ULF protein and that 10–22 activity units for HBGF-0.8-P1 or P2 were recovered after the first HPLC step as compared with 66,666 units in 1 liter of starting material (Table 1). It should be noted that the apparent low recovery of HBGF peptide-0.8 activity was attributable to (i) a major contribution by IGF, EGF, PDGF, bFGF, HB-EGF, and PTN to the overall 3T3 cell mitogenic activity of the crude and partially purified samples (2, 8, 9, 12, 25–27) and (ii) acid lability of HBGF peptide-0.8 mitogenic activity during the HPLC separation step(s). Although alternative strategies were attempted to recover purified growth factors of higher specific activity, it was not possible to avoid the use of either reverse-phase HPLC or trifluoroacetic acid for ion pairing without compromising the purity of the final product. While, in terms of their biological activity, recovery of HBGF-0.8-P1 and -P2 was somewhat compromised, structural characterization of the proteins was readily achieved, since they retained sufficient activity to be unequivocally attributable to a single, homogenous 10-kDa band in SDS-polyacrylamide gels, and sufficient quantities of each protein were isolated from several liters of ULF (Table 1).

TABLE 1

| Purification step | Protein recovered ng | $ED_{50}$[a] ng/ml | Total activity units | Activity recovered | Purification factor |
|---|---|---|---|---|---|
| Crude ULF | 3.4 × 10$^8$ | 25,650 | 66,666 | 100 | |
| BioRex 70 | 2.2 × 10$^7$ | 3825 | 28,649 | 43 | 7 |
| EconoPac Hep HBGF-0.8-P1 | 4.8 × 10$^5$ | 3225 | 744 | 1.1 | 8 |
| TSK-Hep | 2.1 × 10$^5$ | 2230 | 473 | 0.7 | 11 |
| $C_8$HPLC, step 1[d] | 1100 | 250 | 22 | 0.03 | 103 |

TABLE 1-continued

| Purification step | Protein recovered ng | $ED_{50}$[a] ng/ml | Total activity units | Activity recovered | Purification factor |
|---|---|---|---|---|---|
| $C_8$HPLC, step $2^d$ HBGF-0.8-P2 | 100 | 25 | 20 | 0.03 | 1026 |
| TSK-Hep | $2.9 \times 10^4$ | 417 | 347 | 0.5 | 62 |
| $C_8$HPLC[d] | 500 | 250 | 10 | 0.015 | 103 |

[a]Concentration of HBFG-0.8 preparation required to give 50% maximal DNA synthesis.
[b]1 unit of activity is the quantity of HBGF-0.8 required to give the $ED_{50}$.
[c]Compared with crude ULF.
[d]Bioactivity diminished due to acid exposure.

EXAMPLE 2

HBGF Polypeptide Sequencing

Fractions containing the HPLC purified growth factors were pooled, dried, and subjected to preparative SDS-PAGE. Proteins in the gel were transferred for 90 min. at 300 mA to a polvinylidene difluoride membrane using 10 mM CAPS buffer (pH 11). The location of the proteins of interest was determined by staining the blots with 0.1% Coomassie R250 in 50% methanol for 2 min, followed by destaining with 50% methanol, 10% acetic acid. Half of each 10-kDa protein band was excised and submitted for N-terminal amino acid sequencing on a model 470A gas phase sequenator (Applied BioSystems, Foster City, Calif.). Phenylthiohydantoin-derivatives were identified by $C_{18}$ reverse phase HPLC. A 16-residue sequence was obtained for HBGF-0.8-P1 with an undetermined residue at position 10, and a 12-residue sequence was obtained for HBGF-0.8-P2 with an undetermined residue at position 9 (Table 2). These data showed that HBGF-0.8-P1 and -P2 were N-terminally identical except for the presence of an additional Glu residue at the N terminus of HBGF-0.8-P1. A search of GenBank™ revealed that these sequences aligned perfectly with predicted internal sequences of hCTGF and mouse fisp-12 (also termed βIG-M2), the murine homologue of CTGF (Bradham, D. M., et al., (1991) *J. Cell Biol.* 114, 1285–1294; Ryseck, R-P., et al., (1991) *Cell Growth Differ.* 2, 225–233; Brunner, A., et al., (1991) *DNA Cell Biol.* 10, 293–300). The unassigned residue in cycle 10 of HBGF-0.8-P1 and cycle 9 of HBGF-0.8-P2 corresponded to $Cys^{256}$ of hCTGF and $Cys^{255}$ of fisp-12 (Table 2).

To verify that the partial sequences of HBGF-0.8-P1 and -P2 were actually present in the porcine CTGF (pCTGF) molecule, a full-length pCTGF cDNA was isolated by hybridization screening of a pig endometrial cDNA library using a $^{32}$P-labeled hCTGF probe. For these studies, total pig endometrial RNA was obtained as described (Kim, G. Y., et al., (*Biol. Reprod.* 52, 561–571 (1995)). A poly(A)Tract mRNA isolation system (Promega, Madison, Wis.) was used to isolate poly($A^+$) RNA, 5 µg of which was subjected to first strand cDNA synthesis using Moloney murine leukemia virus reverse transcriptase and oligo(dT) linker-primer containing XhoI. Second strand synthesis was primed by treating the mRNA-cDNA complex with RNase. Double-stranded cDNA was blunted using Klenow fragment and ligated to EcoRI adaptors that were subsequently phosphorylated with T4 polynucleotide kinase. 100 ng of XhoI-digested cDNA, purified on a Sephacryl S-400 column, were ligated into 1 µg of Uni-ZAP XR vector arms at the XhoI-EcoRI multiple cloning site, and the product was packaged using Gigapack II packaging extract (Stratagene, La Jolla, Calif.). The primary library was amplified in XL1-Blue MRF' cells to a titer of $1.4 \times 10^{10}$ plaque-forming units/ml.

A verified $^{32}$P-labeled CTGF probe, corresponding to the 3' end of the predicted hCTGF primary translational product, was obtained by reverse transcriptase-polymerase chain reaction of RNA from human foreskin fibroblasts using the forward and reverse primers, 5'-GCCGTCTAG AGCGGCCGCATGGAAGAGAACATTAAGAAGGG-3' (SEQ ID NO:3) and 3'-CCTCTGTACCGTACTTAAGCG CCGGCGACC-5' (SEQ ID NO:4), respectively. The probe was used to screen $10^6$ plaques, two of which showed reproducible hybridization and were isolated using a Rapid Excision Kit (Stratagene). Two ~5.0-kilo-basepair pBluescript SK pig CTGF clones, termed pBSK-pBSK-pCTGF1 and pBSK-p-pCTGF2, were obtained and used for initial sequencing reactions. pBSK-pCTGF1 was then fully sequenced by a combination of manual and automated dideoxy terminator sequencing (Sanger, F., et al., *Proc. Natl.*

TABLE 2

| HBGF-0.8-P1[a] (SEQ ID NO:1) | Glu—Glu—Asn—Ile—Lys—Lys—Gly—Lys—Lys—Xaa—Ile—Arg—Thr—Pro—Lys—Ile |
|---|---|
| HBGF-0.8-P2[b] (SEQ ID NO:2) | Glu—Asn—Ile—Lys—Lys—Gly—Lys—Lys—Xaa—Ile—Arg—Thr |
| Human CTGF-(247–262)[c] | Glu—Glu—Asn—Ile—Lys—Lys—Gly—Lys—Lys—Cys—Ile—Arg—Thr—Pro—Lys—Ile |
| fisp-12-(246–261)[d] | Glu—Glu—Asn—Ile—Lys—Lys—Gly—Lys—Lys—Cys—Ile—Arg—Thr—Pro—Lys—Ile |
| Porcine CTGF-(247–262)[e] | Glu—Glu—Asn—Ile—Lys—Lys—Gly—Lys—Lys—Cys—Ile—Arg—Thr—Pro—Lys—Ile |

[a]Repetitive yield = 88%; initial yield - 7 pmol.
[b]Repetitive yield = 90%; initial yield - 3 pmol.
[c]See Bradham et al. J. Cell Biol. 114:1285–1294, 1991.
[d]See Ryseck et al. Cell Growth Differ. 2:225–233, 1991.
[e]From cDNA analysis in this study.

*Acad. Sci.* U.S.A. 74, 5463–5467 (1977)). Sequence data were obtained from both strands of DNA. Sequences of HBGF0.8-P1 and -P2 are listed in Table 2.

The cloned pig CTGF cDNA was determined to be 1.51 kilobase pairs, with an open reading frame of 1,047 base pairs. The primary translational product of pCTGF is predicted to comprise 349 amino acids and contains HBGF peptide-0.8 sequence between residues 247 and 262 (Table 2). At the amino acid level, pCTGF is approximately ~92% identical to fisp-12 and hCTGF. After cleavage of its presumptive 26-residue signal peptide, pCTGF is predicted to comprise 323 amino acids and to contain 38 Cys residues that are fully conserved in hCTGF and fisp-12.

EXAMPLE 3

HBGF Antibody Production

Since HBGFs represent microheterogenous forms of truncated CTGF, the relationship of HBGF to CTGF was investigated. The presence of the 10-kDa protein in the starting material was confirmed by Western blotting of unfractionated ULF samples using a CTGF antibody that reacted with HPLC-purified HBGF polypeptides.

To produce the antibody, a four-branched multiple antigenic CTGF-(247–260) peptide comprising the sequence EENIKKGKKCIRTP (residues 247–260) (SEQ ID NO:5) was produced on a Synergy 432A peptide synthesizer (Applied BioSystems) and purified by reverse-phase HPLC using a $C_{18}$ column (0.46×36 cm; Rainin Instruments) that was developed with a 90-min 5–95% acetonitrile gradient in water, 0.1% trifluoroacetic acid. Fractions containing the purified polypeptides were pooled, evaporated to dryness, and reconstituted in sterile water. Two New Zealand White rabbits (rabbits A and B), which had been bled to collect preimmune serum, were injected subcutaneously with 1 mg of polypeptide in Freund's complete adjuvant, followed 3 weeks later by an intramuscular injection of 250 µg of polypeptide in Freund's incomplete adjuvant. Animals were bled 7 days later for collection of antiserum. Reactivity of the antisera was validated by Western blotting and immunoprecipitation. Pre-immune serum and antiserum from rabbit A were used in these experiments.

EXAMPLE 4

Generation of the 10-kDa HBGF Polypeptides

Western blotting was performed as has been previously described (Harlow and Lane, 1988, *Antibodies, A Laboratory Manual*, Cold Spring Harbor Laboratory, New York, Current Edition). Briefly, SDS-PAGE was performed under reducing conditions using 18% polyacrylamide mini-gels as described (Kim, G. Y., et al., *Biol. Reprod.* 52, 561–571 (1995)). Silver staining of proteins was performed as described (Wray, W., et al., *Anal. Biochem.* 118, 197–203 (1981)). Western blotting was performed on (i) HPLC-purified growth factors, (ii) 8 µl of unfractionated ULF, or (iii) 100 µl of ULF after passage through 20-µl beds of heparin-Sepharose in the presence of 10 mM Tris-HCl, 0.5M NaCl (pH 7.4) and subsequent extraction of the heparin beads with SDS-PAGE sample buffer. Gels were blotted and blocked as described (Kim, G. Y.,et al., *Biol. Reprod.* 52, 561–571 (1995)) and incubated with a 1:1,000 dilution of rabbit preimmune serum or a 1:1,00 dilution of rabbit anti-pCTGF-(247–260) peptide antiserum (rabbit A). Immunoreactive bands were visualized using alkaline phosphatase-conjugated goat anti-rabbit IgG followed by nitro blue tetrazolium/5-bromo-4-chloro-3-indolyl phosphate chromogenic substrates.

In addition to the 10-kDa protein, two additional mass forms of CTGF (16 and 20-kDa) were also present in ULF, but convincing evidence for the 38-kDa CTGF was not obtained. The Western blot further verified that HPLC purified HBGF comprised a single immunoreactive 10-kDa protein. Comparison of the staining intensity of HBGF from defined volumes of undiluted uterine fluid (i.e. 0.7–2.3 µl) with the staining intensity of mitogenic amounts of purified HGBF indicated that mitogenic concentrations of HBGFs exist in uterine fluid in vivo. Taken together, the data showing that ULF did not contain detectable levels of 38-kDa CTGF but did contain HBGFs in amounts likely to be mitogenic, demonstrate that HBGFs occur naturally in vivo and is not the result of a breakdown of 38 kDa CTGF during their purification.

EXAMPLE 5

Heparin Binding Properties of HBGF Polypeptides

The presence of an additional acidic Glu residue at the N-terminus of HBGF polypeptide 0.8-P1 was correlated with the lower heparin affinity of this molecule as compared with HBGF-0.8-P2, suggesting that the N-terminus of HBGF peptide-0.8 may be part of a heparin-binding domain. To test the heparin-binding properties of the N-terminal region as well as other portions of the CTGF molecule, the ability of 18 polypeptides spanning the entire C-terminal 103 residues of hCTGF to bind [$^3$H]heparin was investigated.

Eighteen synthetic polypeptides spanning the entire 103 C-terminal residues of CTGF were synthesized and received as a cleaved PepSet™ from Chiron Mimotopes (Clayton, Victoria, Australia). All polypeptides were synthesized with acetylated N-termini and amidated C-termini except CTGF-(247–255) and CTGF-(247–260), which were synthesized with free N-terminal amines, and CTGF-(326–349) and CTGF-(339–349), which were synthesized with acid C-termini (Table 3).

All polypeptides contained one or no Cys residues; $Cys^{292}$ in CTGF(285–292) and $Cys^{325}$ in CTGF-(318–328) were replaced with Ser to prevent intra-chain disulfide bridging to $Cys^{287}$ or $Cys^{323}$ within the respective polypeptides. Heparin-binding properties were determined using an adaptation of the method of Baird et al. (Baird, A., et al. *Proc. Natl. Acad. Sci.* U.S.A. 85, 2324–2328 (1988)). Briefly, 37.5 nmol of each polypeptide were absorbed in duplicate to nitrocellulose using a dot-blot apparatus. The blot was blocked for 30 min. with 100 mM Tris-HCl, 0.15M NaCl, 0.1% bovine serum albunin (pH 7.4) and then incubated for 3 hr. at room temperature in this solution containing 10 µCi/ml [$^3$H]heparin (NEN Life Science Products). The blot was washed four times with 10 mM Tris-HCl, 0.15M NaCl, and individual dots were mixed with scintillation fluid for counting of [$^3$H].

Table 3 summarizes the results obtained with the synthetic polypeptides. The highest level of heparin binding was obtained for polypeptides containing residues 247–260, 274–286, and 305–328. It should be noted that none of these polypeptides had HBGF polypeptide agonist or antagonist activity in a 3T3 cell DNA synthesis assay.

TABLE 3

| Peptide domain | Sequence | [³H] Heparin bound (mean ± S.D.) cpm/μg |
|---|---|---|
| None | | 11 ± 0.2 |
| CTGF-(247–255) | EENIKKGKK[a] | 10 ± 0.3 |
| CTGF-(247–260) | EENIKKGKKCIRTP[a] | 836 ± 1 |
| CTGF-(257–272) | IRTPKISKPIKFELSG | 70 ± 13 |
| CTGF-(259–275) | TPKISKPIKFELSGCTS | 124 ± 3 |
| CTGF-(274–283) | TSMKTYRAKF | 388 ± 12 |
| CTGF-(274–286) | TSMKTYRAKFCGV | 1108 ± 119 |
| CTGF-(285–291) | GVCTDGR | 7 ± 0.3 |
| Ser$^{292}$ CTGF-(285–292) | GVCTDGRS | 8 ± 0.4 |
| CTGF-(293–306) | CTPHRTTTLPVEFK | 9 ± 1.1 |
| CTGF-(294–306) | TPHRTTTLPVEFK | 11 ± 0.4 |
| CTGF-(305–322) | FKCPDGEVMKKNMMFIKT | 237 ± 22 |
| CTGF-(308–322) | PDGEVMKKNMMFIKT | 71 ± 2 |
| CTGF-(318–324) | MFIKTCA | 475 ± 116 |
| Ser$^{325}$ CTGF-(318–328) | MFIKTCASHYN | 601 ± 40 |
| CTGF-(324–328) | ACHYN | 9 ± 1 |
| CTGF-(326–349) | HYNCPGDNDIFESLYYRKMYGDMA[b] | 10 ± 1 |
| CTGF-(330–340) | PGDNDIFESLY | 10 ± 0.5 |
| CTGF-(339–349) | LYYRKMYGDMA[b] | 9 ± 0.5 |

[a]Free N-terminal amine.
[b]Acid C teminus

Previous studies have shown that heparin modulates receptor binding and biological activity of several HBGF polypeptides including bFGF, HB-EGF, and amphiregulin (Besner, G. E., et al., *Growth Factors* 7, 289–296 (1992); Higashiyama, S., et al., *J. Cell Biol.*, 122, 933–940 (1993); Rapraeger, A. C., et al., *Science* 252, 1705–1708 (1991); Olwin, B. B., et al. *J. Cell Biol.* 118, 631–639 (1992); Cook, P., et al. *J. Cell Physio.* 163, 418–429 (1995); Yayon, A., et al., *Cell* 64, 841–848 (1991); Aviezer, D., et al. *Proc. Natl. Acad. Sci. U.S.A.* 91, 12173–12177 (1994)). Since HBGF peptide-0.8 exhibited strong affinity for heparin, we examined the effect of this glycosaminoglycan on the mitogenic activity of HBGF peptide-0.8. The activity of a high stimulatory dose of HBGF peptide-0.8 was significantly potentiated by 1–3 μg/ml heparin but was inhibited by 30–100 μg/ml heparin. The same heparin dosages had no effect on basal or calf serum-stimulated DNA synthesis in 3T3 cells.

EXAMPLE 6

HBGF Mitogenic Assay

To assess the relative mitogenic capability of HBGFs with IGF-1, EGF, bFGF, and PDGF-AB, DNA synthesis assays on 3T3 cells were performed (Table 4). Biologically active fractions containing the 0.3–0.6M NaCl eluate from the Bio-Rex column were pooled, diluted 3-fold with 20 mM Tris-HCL (pH 7.4) containing 0.1% CHAPS, passed through a 0.45-μm membrane filter, placed in a siliconized polypropylene vessel, and applied with a peristaltic pump to an EconoPac heparin column (0.7×3.6 cm; Bio-Rad) at 2 ml/min. The heparin column was then washed with 50 ml of 20 mM Tris-HCl buffer, 0.2M NaCl, 0.1% CHAPS and developed at 1 ml/min with a 40 ml gradient of 0.1–2.0M NaCl in 20 mM Tris-HCl, 0.1% CHAPS (pH 7.4) using a fast protein liquid chromatography (FPLC) system (Pharmacia Biotech Inc.). Fractions (1 ml) were collected into siliconized tubes during NaCl gradient elution and tested for 3T3 cell mitogenic activity.

Column fractions were tested for their ability to stimulate DNA synthesis as measured by [³H]thymidine incorporation into the DNA of confluent quiescent Balb/c 3T3 cells grown in 200 μl of Dulbecco's modified Eagle's medium, 10% bovine calf serum in 96-well culture plates as described (Kim, G. Y., et al., *Biol. Reprod.* 52, 561–571 (1995)). Dose-response curves to purified growth factors from ULF were established by assaying each dose in triplicate, with data computed as mean±S.D. Statistical significance of the effects of 1–100 μg/ml porcine heparin (Sigma) on growth factor activity was determined by Students' t test.

[³H] thymidine incorporation by HBGF peptide was comparable with that of calf serum or purified PDGF or bFGF rather than that of weaker mitogens such as IGF or EGF. Further, it was found that the 3T3 mitogenic and biologic activity of HBGFs was synergistically potentiated by 10 ng/ml IGF-I, 10 ng/ml PDGF, 3 ng/ml EGF, or 0.3 ng/ml bFGF.

Target cell specificity was studied using Balb/c 3T3 cells, bovine capillary endothelial cells (BCECs), and vascular smooth muscle cells. 3T3 cells were utilized as described above.

BCECs were obtained from Dr. J. Folkman (Children's Hospital, Boston, Mass.) and were maintained in gelatinized culture flasks in Dulbecco's modified Eagle's medium containing 3 ng/ml bFGF and 10% heat-inactivated bovine calf serum. Smooth muscle cells were isolated from a 2–3-cm length of pig thoracic aorta using established procedures (Weich, H. A., et al., *Growth Factors* 2, 313–320 (1990)) and maintained in 10% Dulbecco's modified Eagle's medium, 10% fetal bovine serum. BCEC and smooth muscle cell DNA synthesis assays were performed in 48- or 96-well plates essentially as described (Besner, G. E., Higashiyama, S., and Kagsbrun, M. *Cell Regul.* 1, 811–819 (1990)). BCEC DNA synthesis assays were also performed in the presence of 100 μg/ml porcine heparin. HGBF was found to be mitogenic for smooth muscle cells and produced a level of stimulation that exceeded that of a maximal amount of EGF but was less than that of bFGF. HBGFs lacked mitogenic activity for endothelial cells when tested alone or in the presence of 100 μg of heparin (see Table 4).

TABLE 4

| Cell Type | Treatment | [³H] Thymidine incorporation (mean ± S.D.) Cpm/well |
|---|---|---|
| Balb/c 3T3 fibroblasts | None | 428 ± 18 |
| | 20% calf serum | 123,820 ± 7,470 |
| | 30 ng/ml IGF-1 | 4,412 ± 170 |
| | 30 ng/ml EGF | 11,550 ± 101 |
| | 10 ng/ml bFGF | 73,853 ± 3,122 |
| | 30 ng/ml PDGF-AB | 110,110 ± 7,077 |
| | 20 μl/ml HBGF-0.8 | 114,730 ± 3,200 |
| Vascular smooth muscle cells | None | 680 ± 341 |
| | 3 ng/ml EGF | 1,343 ± 378 |
| | 3 ng/ml bFGF | 3,082 ± 374 |
| | 15 μl/ml HBGF-0.8 | 1,709 ± 403 |
| Capillary endothelial cells | None | 316 ± 84 |
| | 100 μg/ml heparin | 240 ± 52 |
| | 3 ng/ml bFGF | 2,865 ± 276 |
| | 3 ng/ml bFGF + 100 μg/ml heparin | 1,840 ± 4 |
| | 3 ng/ml aFGF | 603 ± 46 |
| | 3 ng/ml aFGF + 100 μg/ml heparin | 2,232 ± 236 |
| | 20 μl/ml HBGF-0.8 | 243 ± 4 |
| | 20 μl/ml HBGF-0.8 + 100 μg/ml heparin | 195 ± 12 |

Although the invention has been described with reference to the presently preferred embodiment, it should be understood that various modifications can be made without departing from the spirit of the invention. Accordingly, the invention is limited only by the following claims.

What is claimed is:

1. A substantially pure polypeptide characterized as:
   a) having an amino acid sequence corresponding to the carboxy terminal amino acids of a connective tissue growth factor (CTGF) protein;
   b) binding to heparin and being eluted from heparin with about 0.8M salt; and
   c) having a molecular weight of about 10-kDa by reducing SDS-PAGE.

2. The polypeptide of claim 1, wherein the polypeptide has an amino acid sequence beginning at amino acid residue 247 from the N-terminus of CTGF.

3. The polypeptide of claim 1, wherein the polypeptide has an amino acid sequence beginning at amino acid residue 248 from the N-terminus of CTGF.

4. An isolated polynucleotide sequence encoding a polypeptide having an amino acid sequence as in any of claims 1, 2 or 3.

5. A recombinant expression vector which contains the polynucleotide of claim 4.

6. A host cell which contains the expression vector of claim 5.

7. The host cell of claim 6, which is a prokaryote cell.

8. The host cell of claim 6, which is an eukaryote cell.

9. A pharmaceutical composition comprising a therapeutically effective amount of the HBGF of claim 1 in a pharmaceutically acceptable carrier.

* * * * *

UNITED STATES PATENT AND TRADEMARK OFFICE
CERTIFICATE OF CORRECTION

PATENT NO.    : 5,876,730  
DATED         : March 2, 1999  
INVENTOR(S)   : Brigstock et al.

Page 1 of 1

It is certified that error appears in the above-identified patent and that said Letters Patent is hereby corrected as shown below:

<u>Column 1,</u>  
Following the title, but prior to the FIELD OF THE INVENTION section, please insert the following:

-- GOVERNMENTAL SUPPORT  
This invention was made with government support under Grant No. 5R29HD030334 awarded by the National Institutes of Health (National Institute of Child and Human Development). The United States government has certain rights in this invention. --

Signed and Sealed this

Thirtieth Day of September, 2003

JAMES E. ROGAN  
*Director of the United States Patent and Trademark Office*

SEQUENCE LISTING ( 1 ) GENERAL INFORMATION:

( i i i ) NUMBER OF SEQUENCES: 22

( 2 ) INFORMATION FOR SEQ ID NO:1:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:1:

```
Glu  Glu  Asn  Ile  Lys  Lys  Gly  Lys  Lys  Xaa  Ile  Arg  Thr  Pro  Lys  Ile
 1              5                        10                       15
```

( 2 ) INFORMATION FOR SEQ ID NO:2:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:2:

```
Glu  Asn  Ile  Lys  Lys  Gly  Lys  Lys  Xaa  Ile  Arg  Thr
 1              5                        10
```

( 2 ) INFORMATION FOR SEQ ID NO:3:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: oligonucleotide ( x i ) SEQUENCE DESCRIPTION: SEQ ID NO:3:

```
GCCGTCTAGA  GCGGCCGCAT  GGAAGAGAAC  ATTAAGAAGG  G                    41
```

( 2 ) INFORMATION FOR SEQ ID NO:4:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: oligonucleotide ( x i ) SEQUENCE DESCRIPTION: SEQ ID NO:4:

CCTCTGTACC GTACTTAAGC GCCGGCGACC         30

( 2 ) INFORMATION FOR SEQ ID NO:5:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:5:

Glu Glu Asn Ile Lys Lys Gly Lys Lys Cys Ile Arg Thr Pro
1               5                       10

( 2 ) INFORMATION FOR SEQ ID NO:6:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:6:

Glu Glu Asn Ile Lys Lys Gly Lys Lys
1               5

( 2 ) INFORMATION FOR SEQ ID NO:7:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:7:

Ile Arg Thr Pro Lys Ile Ser Lys Pro Ile Lys Phe Glu Leu Ser Gly
1               5                       10                      15

( 2 ) INFORMATION FOR SEQ ID NO:8:

( i ) SEQUENCE CHARACTERISTICS:
        ( A ) LENGTH: 17 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:8:

Thr Pro Lys Ile Ser Lys Pro Ile Lys Phe Glu Leu Ser Gly Cys Thr
1               5                       10                      15
Ser ( 2 ) INFORMATION FOR SEQ ID NO:9:

( i ) SEQUENCE CHARACTERISTICS:
 ( A ) LENGTH: 10 amino acids
 ( B ) TYPE: amino acid
 ( D ) TOPOLOGY: linear ( i i ) MOLECULE TYPE: peptide ( x i ) SEQUENCE DESCRIPTION: SEQ ID NO:9:

Thr Ser Met Lys Thr Tyr Arg Ala Lys Phe
1               5                   10

( 2 ) INFORMATION FOR SEQ ID NO:10:

( i ) SEQUENCE CHARACTERISTICS:
  ( A ) LENGTH: 13 amino acids
  ( B ) TYPE: amino acid
  ( D ) TOPOLOGY: linear ( i i ) MOLECULE TYPE: peptide ( x i ) SEQUENCE DESCRIPTION: SEQ ID NO:10:

Thr Ser Met Lys Thr Tyr Arg Ala Lys Phe Cys Gly Val
1               5                   10

( 2 ) INFORMATION FOR SEQ ID NO:11:

( i ) SEQUENCE CHARACTERISTICS:
  ( A ) LENGTH: 7 amino acids
  ( B ) TYPE: amino acid
  ( D ) TOPOLOGY: linear ( i i ) MOLECULE TYPE: peptide ( x i ) SEQUENCE DESCRIPTION: SEQ ID NO:11:

Gly Val Cys Thr Asp Gly Arg
1               5

( 2 ) INFORMATION FOR SEQ ID NO:12:

( i ) SEQUENCE CHARACTERISTICS:
  ( A ) LENGTH: 8 amino acids
  ( B ) TYPE: amino acid
  ( D ) TOPOLOGY: linear ( i i ) MOLECULE TYPE: peptide ( x i ) SEQUENCE DESCRIPTION: SEQ ID NO:12:

Gly Val Cys Thr Asp Gly Arg Ser
1               5

( 2 ) INFORMATION FOR SEQ ID NO:13:

( i ) SEQUENCE CHARACTERISTICS:
  ( A ) LENGTH: 14 amino acids
  ( B ) TYPE: amino acid
  ( D ) TOPOLOGY: linear ( i i ) MOLECULE TYPE: peptide ( x i ) SEQUENCE DESCRIPTION: SEQ ID NO:13:

Cys Thr Pro His Arg Thr Thr Thr Leu Pro Val Glu Phe Lys
1               5                   10

( 2 ) INFORMATION FOR SEQ ID NO:14:

( i ) SEQUENCE CHARACTERISTICS:
  ( A ) LENGTH: 13 amino acids
  ( B ) TYPE: amino acid
  ( D ) TOPOLOGY: linear ( i i ) MOLECULE TYPE: peptide ( x i ) SEQUENCE DESCRIPTION: SEQ ID NO:14:

Thr Pro His Arg Thr Thr Thr Leu Pro Val Glu Phe Lys
 1               5                   1 0

( 2 ) INFORMATION FOR SEQ ID NO:15:

( i ) SEQUENCE CHARACTERISTICS:
        ( A ) LENGTH: 18 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:15:

Phe Lys Cys Pro Asp Gly Glu Val Met Lys Lys Asn Met Met Phe Ile
 1               5                   1 0                         1 5

Lys Thr ( 2 ) INFORMATION FOR SEQ ID NO:16:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:16:

Pro Asp Gly Glu Val Met Lys Lys Asn Met Met Phe Ile Lys Thr
 1               5                   1 0                     1 5

( 2 ) INFORMATION FOR SEQ ID NO:17:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:17:

Met Phe Ile Lys Thr Cys Ala
 1               5

( 2 ) INFORMATION FOR SEQ ID NO:18:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:18:

Met Lys Ile Lys Thr Cys Ala Ser His Tyr Asn
 1               5                   1 0

( 2 ) INFORMATION FOR SEQ ID NO:19:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide (x i) SEQUENCE DESCRIPTION: SEQ ID NO:19:

Ala Cys His Tyr Asn
1               5

(2) INFORMATION FOR SEQ ID NO:20:

(i) SEQUENCE CHARACTERISTICS:
(A) LENGTH: 24 amino acids
(B) TYPE: amino acid
(D) TOPOLOGY: linear (ii) MOLECULE TYPE: peptide (x i) SEQUENCE DESCRIPTION: SEQ ID NO:20:

His Tyr Asn Cys Pro Gly Asp Asn Asp Ile Phe Glu Ser Leu Tyr Tyr
1               5                   10                  15
Arg Lys Met Tyr Gly Asp Met Ala
            20

(2) INFORMATION FOR SEQ ID NO:21:

(i) SEQUENCE CHARACTERISTICS:
(A) LENGTH: 11 amino acids
(B) TYPE: amino acid
(D) TOPOLOGY: linear (ii) MOLECULE TYPE: peptide (x i) SEQUENCE DESCRIPTION: SEQ ID NO:21:

Pro Gly Asp Asn Asp Ile Phe Glu Ser Leu Tyr
1               5                   10

(2) INFORMATION FOR SEQ ID NO:22:

(i) SEQUENCE CHARACTERISTICS:
(A) LENGTH: 11 amino acids
(B) TYPE: amino acid
(D) TOPOLOGY: linear (ii) MOLECULE TYPE: peptide (x i) SEQUENCE DESCRIPTION: SEQ ID NO:22:

Leu Tyr Tyr Arg Lys Met Tyr Gly Asp Met Ala
1               5                   10